United States Patent
Sarfarazi

(10) Patent No.: US 9,149,356 B2
(45) Date of Patent: *Oct. 6, 2015

(54) INTERIOR BAG FOR A CAPSULAR BAG AND INJECTOR

(71) Applicant: Faezeh Mona Sarfarazi, Encinitas, CA (US)

(72) Inventor: Faezeh Mona Sarfarazi, Encinitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/054,129

(22) Filed: Oct. 15, 2013

(65) Prior Publication Data

US 2014/0046438 A1  Feb. 13, 2014

Related U.S. Application Data

(63) Continuation of application No. 11/653,084, filed on Jan. 12, 2007, now Pat. No. 8,556,967.

(51) Int. Cl.
*A61F 2/14* (2006.01)
*A61F 2/16* (2006.01)

(52) U.S. Cl.
CPC ............... *A61F 2/14* (2013.01); *A61F 2/1662* (2013.01); *A61F 2/16* (2013.01); *A61F 2/167* (2013.01); *A61F 2/16015* (2015.04); *A61F 2/1664* (2013.01); *A61F 2/1678* (2013.01); *A61F 2002/169* (2015.04); *A61F 2002/16902* (2015.04)

(58) Field of Classification Search
USPC .............. 623/4.1, 6.13, 6.34, 6.37, 6.39
See application file for complete search history.

(56) References Cited

U.S. PATENT DOCUMENTS

| | | |
|---|---|---|
| 2,492,458 A | 12/1949 | Bering, Jr. |
| 2,814,294 A | 11/1957 | Figge |
| 3,438,374 A | 4/1969 | Falb et al. |
| 3,698,395 A | 10/1972 | Hasson |
| 3,906,551 A | 9/1975 | Otter |
| 3,925,825 A | 12/1975 | Richards et al. |
| 3,971,073 A | 7/1976 | Richards et al. |
| 3,971,841 A | 7/1976 | Rubinstein |
| 3,995,641 A | 12/1976 | Kronenthal et al. |
| 4,035,334 A | 7/1977 | Davydov et al. |
| 4,079,470 A | 3/1978 | Deeg et al. |
| 4,124,905 A | 11/1978 | Clark |
| 4,172,297 A | 10/1979 | Schlegel |

(Continued)

FOREIGN PATENT DOCUMENTS

| | | |
|---|---|---|
| DE | 19501444 | 7/1996 |
| EP | 0162573 | 11/1985 |

(Continued)

OTHER PUBLICATIONS

Cimberle, Michela, "Three accommodative IOLs show high-quality surface on SEM," Ocular Surgery News U.S. Edition, Aug. 15, 2002, p. 1-3.

(Continued)

*Primary Examiner* — David H Willse
*Assistant Examiner* — Tiffany Shipmon
(74) *Attorney, Agent, or Firm* — Onello & Mello, LLP.

(57) ABSTRACT

An interior bag for a capsular bag of an eye comprises a discriminatingly permeable interior bag that selectively reduces fluid flow volume through the interior bag. The interior bag is secured inside the capsular bag. A structure, adapted to hold a refractive device, is attached to the interior bag.

20 Claims, 5 Drawing Sheets

(56) References Cited

U.S. PATENT DOCUMENTS

| | | |
|---|---|---|
| 4,177,526 A | 12/1979 | Kuppinger et al. |
| 4,206,518 A | 6/1980 | Jardon et al. |
| 4,240,163 A | 12/1980 | Galin |
| 4,253,199 A | 3/1981 | Banko |
| 4,254,509 A | 3/1981 | Tennant |
| 4,271,841 A | 6/1981 | Friedman |
| 4,298,996 A | 11/1981 | Barnet |
| 4,373,218 A | 2/1983 | Schachar |
| 4,409,691 A | 10/1983 | Levy |
| 4,414,976 A | 11/1983 | Schwarz et al. |
| 4,424,597 A | 1/1984 | Schlegel |
| 4,426,741 A | 1/1984 | Bittner |
| 4,427,651 A | 1/1984 | Stroetmann |
| 4,463,458 A | 8/1984 | Seidner |
| 4,466,705 A | 8/1984 | Michelson |
| 4,467,805 A | 8/1984 | Fukuda |
| 4,485,598 A | 12/1984 | Guardiani |
| 4,517,138 A | 5/1985 | Rawlings et al. |
| 4,517,139 A | 5/1985 | Rawlings et al. |
| 4,556,998 A | 12/1985 | Siepser |
| 4,575,373 A | 3/1986 | Johnson |
| 4,603,697 A | 8/1986 | Kamerling |
| 4,605,409 A | 8/1986 | Kelman |
| 4,627,879 A | 12/1986 | Rose et al. |
| 4,664,666 A | 5/1987 | Barrett |
| 4,666,445 A | 5/1987 | Tillay |
| 4,680,149 A | 7/1987 | Rawlings et al. |
| 4,683,142 A | 7/1987 | Zimmermann et al. |
| 4,685,922 A | 8/1987 | Peyman |
| 4,710,193 A | 12/1987 | Volk |
| 4,719,917 A | 1/1988 | Barrows et al. |
| 4,720,286 A | 1/1988 | Bailey et al. |
| 4,725,279 A | 2/1988 | Woodroof |
| 4,750,904 A | 6/1988 | Price, Jr. |
| 4,764,169 A | 8/1988 | Grendahl |
| 4,764,198 A | 8/1988 | Lythgoe |
| 4,790,847 A | 12/1988 | Woods |
| 4,816,031 A | 3/1989 | Pfoff |
| 4,836,960 A | 6/1989 | Spector et al. |
| 4,842,601 A | 6/1989 | Smith |
| 4,883,485 A | 11/1989 | Patel |
| 4,888,012 A | 12/1989 | Horn et al. |
| 4,892,543 A | 1/1990 | Turley |
| 4,902,293 A | 2/1990 | Feaster |
| 4,909,251 A | 3/1990 | Seelich |
| 4,924,866 A | 5/1990 | Yoon |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,976,732 A | 12/1990 | Vorosmarthy |
| 4,989,605 A | 2/1991 | Rossen |
| 4,994,080 A | 2/1991 | Shepard |
| 4,994,082 A | 2/1991 | Richards et al. |
| 5,035,710 A | 7/1991 | Nakada et al. |
| 5,047,051 A | 9/1991 | Cumming |
| 5,076,683 A | 12/1991 | Glick |
| 5,091,121 A | 2/1992 | Nakada et al. |
| 5,108,429 A | 4/1992 | Wiley |
| 5,109,846 A | 5/1992 | Thomas |
| 5,123,905 A | 6/1992 | Kelman |
| 5,152,789 A | 10/1992 | Willis |
| 5,156,613 A | 10/1992 | Sawyer |
| 5,171,320 A | 12/1992 | Nishi |
| 5,173,723 A | 12/1992 | Volk |
| 5,190,057 A | 3/1993 | Sarfarazi |
| 5,201,762 A | 4/1993 | Hauber |
| 5,203,788 A | 4/1993 | Wiley |
| 5,275,623 A | 1/1994 | Sarfarazi |
| 5,275,624 A | 1/1994 | Hara et al. |
| 5,300,262 A | 4/1994 | Glick |
| 5,304,561 A | 4/1994 | Sarfarazi |
| 5,326,347 A | 7/1994 | Cumming |
| 5,360,438 A | 11/1994 | Fisher |
| 5,376,115 A | 12/1994 | Jansen |
| 5,383,898 A | 1/1995 | Sarfarazi |
| 5,391,202 A | 2/1995 | Lipshitz et al. |
| RE34,998 E | 7/1995 | Langerman |
| 5,433,745 A | 7/1995 | Graham et al. |
| 5,476,512 A | 12/1995 | Sarfarazi |
| 5,476,514 A | 12/1995 | Cumming |
| 5,489,299 A | 2/1996 | Schachar |
| 5,489,302 A | 2/1996 | Skottun |
| 5,496,355 A | 3/1996 | Lipsky |
| 5,496,366 A | 3/1996 | Cumming |
| 5,593,436 A | 1/1997 | Langerman |
| 5,607,472 A | 3/1997 | Thompson |
| 5,620,720 A | 4/1997 | Glick et al. |
| 5,628,795 A | 5/1997 | Langerman |
| 5,674,282 A | 10/1997 | Cumming |
| 5,728,155 A | 3/1998 | Anello et al. |
| 5,762,836 A | 6/1998 | Bos et al. |
| 5,769,890 A | 6/1998 | McDonald |
| 5,782,894 A | 7/1998 | Israel |
| 5,843,188 A | 12/1998 | McDonald |
| 5,904,746 A | 5/1999 | Okada |
| 6,013,101 A | 1/2000 | Israel |
| 6,051,024 A | 4/2000 | Cumming |
| 6,096,078 A | 8/2000 | McDonald |
| 6,117,171 A | 9/2000 | Skottun |
| 6,136,026 A | 10/2000 | Israel |
| 6,176,878 B1 | 1/2001 | Gwon et al. |
| 6,193,750 B1 | 2/2001 | Cumming |
| 6,197,059 B1 | 3/2001 | Cumming |
| 6,200,342 B1 | 3/2001 | Tassignon |
| 6,210,610 B1 | 4/2001 | Saito et al. |
| 6,217,612 B1 | 4/2001 | Woods |
| 6,231,603 B1 | 5/2001 | Lang et al. |
| 6,299,641 B1 | 10/2001 | Woods |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,413,276 B1 | 7/2002 | Werblin |
| 6,423,094 B1 | 7/2002 | Sarfarazi |
| 6,428,573 B2 | 8/2002 | Barnett |
| 6,428,574 B1 | 8/2002 | Valunin et al. |
| 6,443,985 B1 | 9/2002 | Woods |
| 6,464,725 B2 | 10/2002 | Skotton |
| 6,478,821 B1 | 11/2002 | Laguette et al. |
| 6,485,516 B2 | 11/2002 | Boehm |
| 6,488,708 B2 | 12/2002 | Sarfarazi |
| 6,537,316 B1 | 3/2003 | Chambers |
| 6,551,354 B1 | 4/2003 | Ghazizadeh et al. |
| 6,558,420 B2 | 5/2003 | Green |
| 6,616,691 B1 | 9/2003 | Tran |
| 6,616,692 B1 | 9/2003 | Glick et al. |
| 6,767,363 B1 | 7/2004 | Bandhauer et al. |
| 6,769,900 B2 | 8/2004 | Murphy et al. |
| 6,939,486 B2 | 9/2005 | DeRyke et al. |
| 7,014,641 B2 | 3/2006 | Kobayashi et al. |
| 7,217,112 B2 | 5/2007 | Kyburz et al. |
| 7,485,144 B2 | 2/2009 | Esch |
| 7,662,179 B2 | 2/2010 | Sarfarazi |
| 7,754,113 B2 | 7/2010 | Kyburz et al. |
| 8,556,967 B2 | 10/2013 | Sarfarazi |
| 2001/0001836 A1 | 5/2001 | Cumming |
| 2001/0007513 A1 | 7/2001 | Koshimizu et al. |
| 2002/0002404 A1 | 1/2002 | Sarfarazi |
| 2002/0045937 A1 | 4/2002 | Sarfarazi |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0138141 A1 | 9/2002 | Zadno-Azizi et al. |
| 2002/0161434 A1 | 10/2002 | Laguette et al. |
| 2002/0173847 A1 | 11/2002 | Pham et al. |
| 2003/0018384 A1 | 1/2003 | Valyunin et al. |
| 2003/0060881 A1 | 3/2003 | Glick et al. |
| 2003/0074061 A1 | 4/2003 | Pham et al. |

(56) References Cited

U.S. PATENT DOCUMENTS

| | | |
|---|---|---|
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0130732 A1 | 7/2003 | Sarfarazi |
| 2004/0015236 A1 | 1/2004 | Sarfarazi |
| 2004/0082995 A1 | 4/2004 | Woods |
| 2004/0230300 A1 | 11/2004 | Bandhauer et al. |
| 2004/0238980 A1 | 12/2004 | Kyburz et al. |
| 2005/0060032 A1 | 3/2005 | Magnante et al. |
| 2005/0113911 A1* | 5/2005 | Peyman .......... 623/6.11 |
| 2005/0137703 A1 | 6/2005 | Chen |
| 2005/0186279 A1 | 8/2005 | Guo et al. |
| 2005/0251253 A1* | 11/2005 | Gross .......... 623/6.13 |
| 2006/0100701 A1 | 5/2006 | Esch et al. |
| 2007/0210464 A1 | 9/2007 | Kyburz et al. |
| 2007/0213816 A1 | 9/2007 | Sarfarazi |
| 2010/0211171 A1 | 8/2010 | Sarfarazi |

FOREIGN PATENT DOCUMENTS

| | | |
|---|---|---|
| EP | 0328117 | 8/1989 |
| EP | 0329981 | 8/1989 |
| EP | 0336877 | 10/1989 |
| EP | 0337390 A2 | 10/1989 |
| EP | 0337390 B1 | 10/1989 |
| EP | 0359539 | 3/1990 |
| EP | 0507292 A1 | 10/1992 |
| EP | 0507292 B1 | 10/1992 |
| EP | 0592813 | 4/1994 |
| EP | 0875354 | 11/1998 |
| FR | 2784575 | 4/2000 |
| GB | 2124500 | 2/1984 |
| GB | 2151371 | 7/1985 |
| JP | 1-163031 | 6/1989 |
| JP | 2-126847 | 5/1990 |
| WO | 8707208 | 12/1987 |
| WO | 9616780 | 6/1996 |
| WO | 9920206 | 4/1999 |
| WO | 0066037 | 11/2000 |
| WO | 0066040 | 11/2000 |
| WO | 0078251 | 12/2000 |
| WO | 0134067 | 5/2001 |
| WO | 02071983 | 9/2002 |
| WO | 03000154 A2 | 1/2003 |
| WO | 03000154 A3 | 1/2003 |
| WO | 2004010905 | 2/2004 |
| WO | 2004106045 | 12/2004 |

OTHER PUBLICATIONS

Adler-Grinberg, Deborah, "Questioning Our Classical Understanding of Accommodation and Presbyopia," American Journal of Optometry and Physiological Optics, vol. 63, No. 7, pp. 571-580.

Hara, et al, "Accommodative Intraocular Lens with Spring Action Part 1: Design and Placement in an Excised Animal Eye," Opthalmic Surgery, vol. 21, No. 2, pp. 128-133, Feb. 1990.

Koretz, et al., "How the Human Eye Focuses," Scientific American, Jul. 1988, pp. 92-99.

McLeod, et al., "A dual optic accommodating foldable intraocular lens," Br J Opthalmol, 2003, 87, pp. 1083-1085.

Schachar MD, PHD, Ronald A., "Cause and Treatment of Presbyopia With a Method for Increasing the Amplitude of Accommodation," Ann Opthalmol, Dec. 1992, vol. 24, No. 12, pp. 445-452.

Schachar MD, PHD, Ronald A., et al., "Experimental Support for Schachar's Hypothesis of Accommodation," Ann Opthalmol, Nov. 1993, vol. 25, No. 11, pp. 404-409.

Schachar MD, PHD, Ronald A., "Zonular Function: A New Hypothesis With Clinical Implications," Ann Opthalmol, Mar.-Apr. 1994, vol. 26, No. 2, pp. 36-38.

Rowsey, JJ. et al., "Use of keratoscopy, slit-lamp biomicroscopy, and retinoscopy in the management of astigmatism after penetrating keratoplasty," Abstract, Refract Corneal Surg., Jan.-Feb. 1991.

Hara, et al., "Accommodativeintraocular lens with spring action—part 2: Fixation in the living rabbit," Abstract, Ophthalmic Surg., Sep. 1992.

Markantonio, Julia M., et al. "Lens Cell Populations Studied in Human Donor Capsular Bags with Implanted Intraocular Lenses", Investigative Ophthalmology & Visual Science, Apr. 2000, vol. 41, No. 5, pp. 1130-1141.

* cited by examiner

INTERIOR BAG FOR A CAPSULAR BAG AND INJECTOR

CROSS REFERENCE TO RELATED APPLICATIONS

This application is a continuation application of U.S. Pat. No. 8,556,967, issued on Oct. 15, 2013, which may be related to U.S. patent application Ser. No. 10/307,679 filed Dec. 2, 2002, now U.S. Pat. No. 7,662,179, which was a continuation-in-part of U.S. patent application Ser. No. 09/288,560 filed Apr. 9, 1999, now U.S. Pat. No. 6,488,708, each of which is incorporated herein in its entirety.

FIELD OF THE INVENTION

This invention relates generally to an interior bag for implantation in the natural capsular bag of an eye and an injector therefor and, more particularly, to an apparatus and method for preventing the condition of posterior capsular opacification (PCO), a condition occurring in about 25 percent of cataract surgery patients, and for preventing and/or treating other conditions of the eye.

BACKGROUND OF THE INVENTION

A cataract is a clouding of the lens of the eye, the lens being responsible for focusing and producing sharp images. Cataracts are the leading cause of vision loss among adults 55 and older. Eye injuries, diseases, and certain medications are believed to accelerate the formation of cataracts.

The lens is contained inside the natural capsular bag in a human eye. Alteration of the structure of the lens over time causes lens opacification or clouding, which makes images look blurred or fuzzy. This process is a natural result of aging and can be accelerated due to injury, disease or medication.

PCO can occur after cataract surgery and cause patients to experience symptoms similar to those from the original cataract. During cataract surgery, a patient's natural lens is replaced with a small artificial lens, called an intraocular lens or IOL. Unfortunately, proteins and/or cells, such as lens epithelial cells retained in the capsular bag following surgery, may proliferate and migrate to the posterior surface inside the capsular bag causing PCO, thereby making clarity of vision difficult.

In an effort to treat PCO patients, surgeons have focused on methods of treating the cells on the inside of the capsular bag. Methods used in the past have included lysing, freezing, polishing, and laser treatment. Unfortunately, some of these methods carry a higher risk of developing a retinal detachment in the future. Additionally, some of these methods may also cause the intraocular lens to dislocate and necessitate surgical repositioning and, in unfortunate cases, result in the destruction of the capsular bag. Moreover, each of these methods does not adequately limit future cell formation inside the capsular bag because aqueous humor fluid flow through the capsular bag continues to provide an environment friendly to cell growth or even cell migration into the posterior part of the bag via fluid flow causing PCO. There is a need in the art to provide a means for inhibiting PCO.

There is also a need to provide a means for retaining the shape of the capsular bag and for reducing or eliminating shrinkage of the capsular bag following cataract surgery. In addition, experiments are now underway to inject silicone or other transparent materials into the capsular bag following cataract surgery to form a replacement lens in situ rather than using a conventional IOL and the present invention may facilitate the use of such a lens. The present invention may further provide a reservoir for retaining and releasing a time release pharmaceutical agent for treatment of glaucoma or infection such as iritis or uvitis.

SUMMARY OF THE INVENTION

It is in view of the above problems that the present invention was developed. Generally, the invention is an interior bag for placement in a capsular bag of an eye and an injector for placing the interior bag within the capsular bag. The interior bag is a discriminatingly permeable (or even impermeable) interior bag that reduces aqueous humor fluid flow volume through the capsular bag to provide a less favorable growth environment for cells that cause PCO, that aids in properly positioning an intraocular lens and in maintaining a proper position, and that may aid in removing PCO cellular buildup within the capsular bag. The interior bag may further provide support for the capsular bag to prevent or reduce shrinkage and to maintain the natural shape of the capsular bag following cataract surgery, and provide a reservoir for containing the silicone or other materials used in forming an injectable lens. It may also provide a reservoir for a pharmaceutical agent to treat certain conditions of the eye.

An injector for the interior bag is used to insert the interior bag into the capsular bag. The injector is adapted to hold the interior bag and may also hold an IOL. The injector has a housing that is further adapted to hold a pressurizing fluid in a fluid containment reservoir. A plunger for ejecting a volume of fluid from the fluid containment reservoir is disposed in the housing for ejecting the interior bag with the fluid into the capsular bag of the eye.

A method for inserting an interior bag inside an injector and injecting the interior bag into a capsular bag requires first that an interior bag be inserted or placed into an opening of the housing of the injector. The housing now holds the interior bag and the fluid containment reservoir is empty. Surgical or optical fluid or gel is then placed inside the fluid containment reservoir, in some cases either before or after a refractive device such as an IOL is placed inside the reservoir. The injector is now ready to deploy the interior bag. The interior bag is ejected from the injector by moving the plunger through the reservoir to collapse and invert the interior bag, eject it through an open distal end of the reservoir and fill it with the fluid or gel. A closed system is then created inside the interior bag. Finally, the interior bag is positioned and secured inside the capsular bag.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE INVENTION

Figure 1:
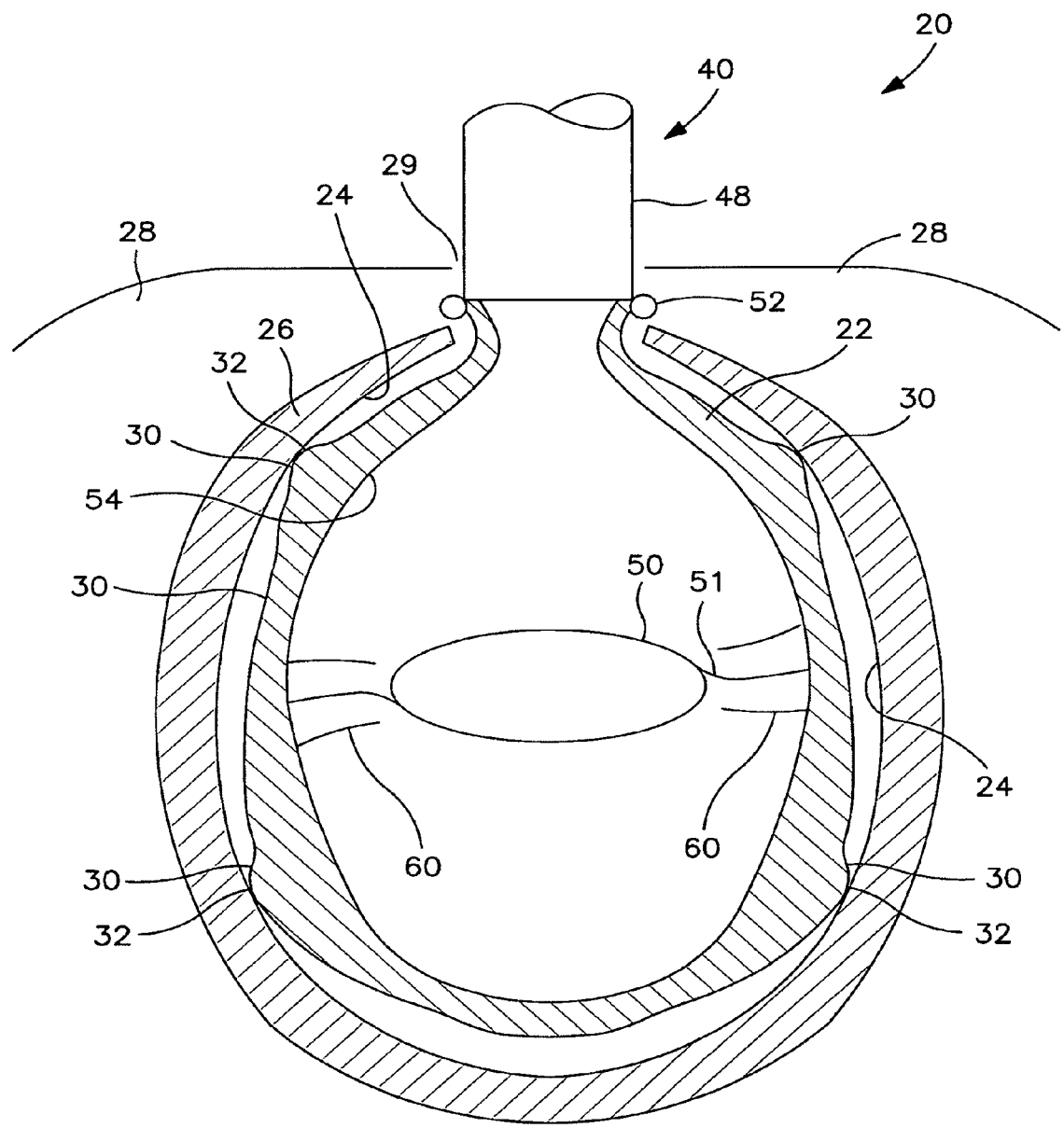
FIG. 1 illustrates a cross-sectional view of an interior bag within a capsular bag and an injector therefore.
Figure 2:
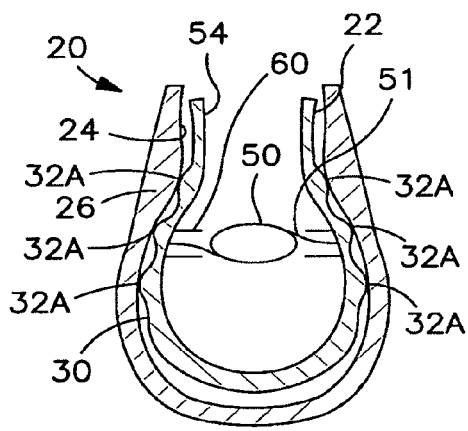
FIGS. 2-6 illustrate cross-sectional views showing different embodiments of the interior bag within the capsular bag.
Figure 3:
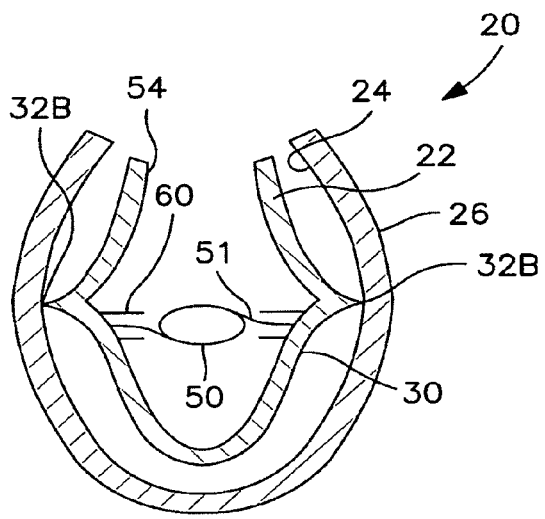
Figure 6:
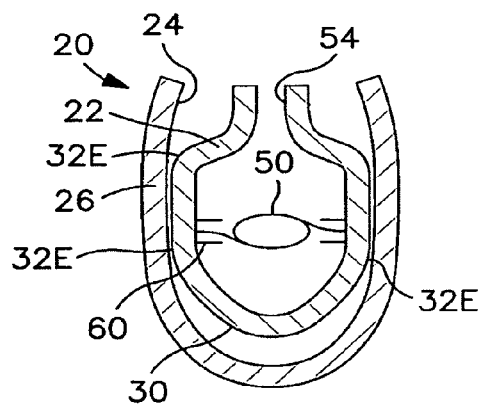
Figure 5:
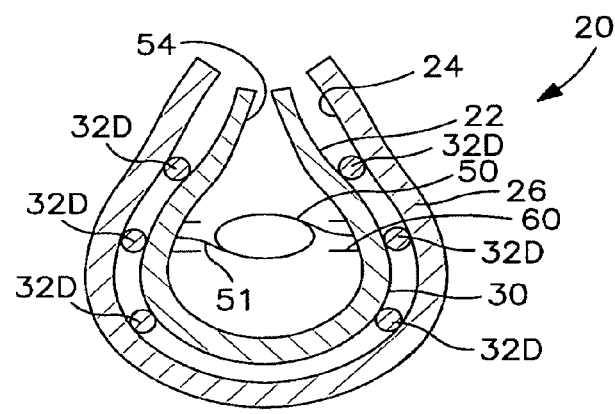
Figure 4:
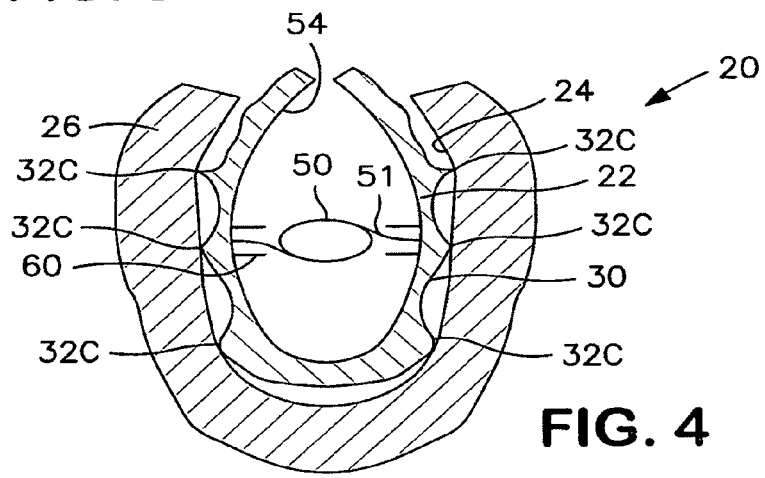

Referring to the accompanying drawings in which like reference numbers indicate like elements, FIG. 1 illustrates one embodiment of the invention shown generally at 20, with an interior bag 22 sized to fit within a natural capsular bag 26 of a human eye 28, the interior bag 22 containing a refractive device 50. The distal end of an injector for the interior bag 22 is shown generally at 40.

The interior bag 22 may be impermeable, semi-permeable or permeable, depending on the desired use and the circumstances of the particular case. Permeability of the interior bag is determined relative to the ability to permit aqueous humor or other fluids to pass through the wall of the interior bag. By its placement within the capsular bag 26, the interior bag 22 occupies a substantial portion of the volume of the capsular bag 26 and thereby inhibits the free flow of floating aqueous humor through the capsular bag 26. The interior bag 22 includes an irregularly contoured outer surface 30. As shown in FIGS. 1-6, the irregularly contoured outer surface 30 may have many different embodiments, with one or more projections 32 used to secure the interior bag 22 to an inside surface 24 of capsular bag 26 and further reduce the flow of aqueous humor. Fixation of the interior bag 22 within the capsular bag 26 may occur through frictional engagement of the projections 32 with the interior surface 24, by the formation of fibrosis between the projections 32 and the inside surface 24, or by a combination of both. The projections 32 may take the form of multiple humps 32A shown in FIG. 2, defined edges or points 32B, possibly formed by crimping, shown in FIG. 3, multiple defined and angled edges 32C shown in FIG. 4, thickened rim areas or beads 32D shown in FIG. 5, or flat sides with corners 32E shown in FIG. 6. The preferred embodiment, as shown in FIG. 1, uses a square-edged outer surface 30. The projections 32 may be positioned to engage the interior surface 24 either at approximately the midpoint, or above and/or below the midpoint, of the capsular bag 26 as this orientation prevents or reduces cell and protein migration toward the posterior inside surface the capsular bag 26, thus reducing the likelihood of PCO.

It is emphasized that projections 32 serve to maintain the interior bag 22 in a relatively constant position with respect to the capsular bag 26. This is a key feature of the present invention. Accordingly, the position of the refractive device 50 may be reliably maintained relative to the capsular bag 26. This eliminates the common problem of a skewed or tilted position of the refractive device 50 within the capsular bag 26 after surgery, which often necessitates another surgery to correct the position of the refractive device 50. In addition, the projections 32 (or projections 32A-32E) maintain a stable position, but as the capsular bag 26 moves, the position of the projections 32 (or projections 32A-32E) also may experience slight displacement along the wall of the capsular bag 26, at least prior to formation of fibrosis. As this occurs, the projections 32 (or projections 32A-32E) may scrub or file the interior surface 24 of the capsular bag 26 of PCO cellular buildup. After fibrosis formation, slight movement may still occur between the projections 32 to scrub the interior surface 24 of capsular bag 26.

The interior bag 22 is a thin, optically clear, biologically compatible, rounded bag (rounded to approximate the dimensions of the capsular bag 26) and is adapted to hold a refractive device 50, such as a compressible disc lens, a traditional lens with two or more haptics or a material forming an injectable lens. The interior bag 22, although being impermeable or semi-permeable to limit the flow of aqueous humor through the capsular bag 26, must be thin and optically clear in order to allow light transmission to the back of the eye 28. In addition, in order to reduce the possibility for rejection, the interior bag 22 must be made of a biologically compatible material and it must be strong enough to protect the refractive device 50 and prevent it from tearing capsular bag 26. Examples of suitable materials are silicones, hydrogels and other materials commonly used in the manufacture of IOLs and other ocular implants.

The reduction of mass flow rate of aqueous humor fluid flow through the capsular bag 26 is important as it limits the deposition of excess proteins inside the capsular bag 26, and even on a refractive device, thus reducing the probability of a patient contracting PCO. Since the interior bag 22 is discriminatingly permeable (not permitting or reducing the flow of aqueous humor through the wall of the interior bag 22), the flow of aqueous humor into the interior bag 22 is also reduced. This is a key feature of the present invention because the aqueous humor transports the cells and proteins that can deposit on the interior of the bag 22 and on refractive device 50 and reduce their light transmitting properties. The interior bag 22, however, still allows sufficient fluid flow inside the capsular bag 26 to permit the capsular bag 26 to continue to receive the nourishment it needs.

As noted, there may be several friction-fitting projections employed on the interior bag 22, for example, projections 32 (or projections 32A-32E). These may, for example, include a single or multiple rims, beads, crimps, points, etc. that extend around a portion or the entire outer periphery of interior bag 22. As such, the number of friction-fitting features used may vary, as conditions require. The only limitations to the friction fitting features is that they assist in maintaining the relative position of the interior bag 22 with respect to the capsular bag 26, and reduce or interrupt aqueous humor flow in the space between the outer surface of interior bag 22 and interior surface 24 of the capsular bag 26 to reduce or eliminate the potential for PCO.

A bridge or support structure 60, adapted to hold a refractive device 50 such as an IOL, is formed inside the interior bag 22. The IOL has haptics 51 that fit between and engage opposed surfaces of the support 60 to hold the IOL 50 securely in place inside the interior bag 22. The refractive device 50 preferably has an index of refraction greater than or equal to a natural human lens. It is understood that the bridge or support structure 60 may be any apparatus that is capable of holding the IOL and is biologically compatible to body. The support structure 60 prevents the tilting of the haptics of the IOL 50, e.g. wherein one haptic can be tilted over the equator, and the other haptic tilted under the equator. It is estimated that eighty percent (80%) of IOLs have some tilting. It is very important to note that while the preferred embodiment places the support structure 60 on the equator, the structure 60 does not have to be placed on the equator of the capsular bag 26 or on the equator of the interior bag 22. Instead, the structure 60 may be in front or in back of the equator to permit accurate adjustment of the power of the IOL based upon the distance between the IOL and the cornea. For example, while high power lenses are available, they are thick and may therefore be undesirable. By proper placement of the structure 60, high power may be achieved using thinner lenses. An estimated additional accommodation of between one and three diopters can be achieved by vitreous pressure in the posterior part of the capsular bag pushing the structure 60 (and thus the position of the refractive device 50) forward. In addition, multiple IOLs, including multifocal and piggyback lenses, could be held by one or more support structures 60 as necessary to obtain higher magnification needed for treating patients, for example, having macular degeneration. Alternatively, an optical fluid or gel may constitute the refractive device, the fluid or gel having an index of refraction of between about 1.43 to 1.46 or such other power of refraction as is necessary to provide acceptable vision. In this case, the optical fluid or gel would be injected directly into and fill the interior bag 22 and the support structure 60 would be eliminated.

Figure 7:
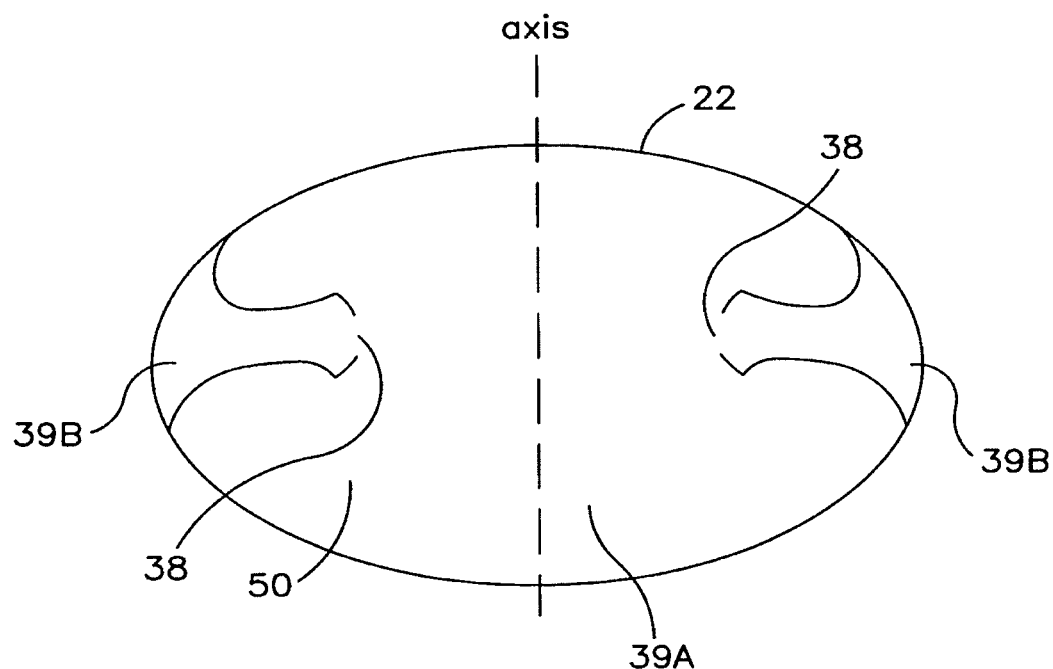
FIG. 7 illustrates a further embodiment of the interior bag showing a secondary chamber for facilitating interior bag movement when changing shape to focus.

Accommodation is the ability of the eye to sharply focus on both near and far objects. With a natural lens, the ciliary muscles, acting through the zonules, cause the capsular bag to flatten or elongate in the direction of the optical axis to change the focal length of the lens to sharply focus an image on the retina irrespective of the distance of the object from the eye. FIG. 7 introduces the concept of an interior bag 22 having multiple chambers, with a main chamber shown generally at 39A and a secondary chamber shown at 39B, to permit accommodation when an optical fluid or gel constitutes the refractive device 50. Specifically, when the refractive device 50 is a gel or other optical fluid lens, there is no need for the support structure 60 and the gel or optical fluid fills the main chamber 39A of the interior bag 22. The gel lens or optical fluid lens filling the main chamber 39A constitutes the refractive device 50. To permit accommodation, the interior bag 22 is adapted to change its shape under forces exerted on it by the capsular bag. The rapidity of the change in shape and therefore focus of the refractive device 50 is defined by the rapidity with which the interior bag 22 can change shape. As shown in FIG. 7, the interior bag 22 is equipped with one or more orifices or other openings 38 that permit fluid flow communication between the main chamber 39A, which is initially filled with the gel or optical fluid, and the secondary chamber 39B, which is initially empty, to permit rapid change in the shape of the interior bag 22. The size of the orifices or openings 38 and the volume of the secondary chamber 39B are dependent on the viscosity of the gel or other optical fluid and the rapidity of interior bag shape change desired. Thus, the interior bag 22 can rapidly flatten along the optical axis when the capsular bag 26 exerts a pulling force, due to contraction of the zonules of zinn during unaccommodation, creating a positive pressure in main chamber 39A and some gel or optical fluid is expelled through the orifices 38 into the secondary chamber 39B of the interior bag 22. During accommodation, when a more elongate shape along the optical axis is desired, the capsular bag 26 exerts a relaxing force on the interior bag 22 creating a negative pressure in main chamber 39A and some gel or fluid is forced or drawn from the secondary chamber 39B into the main chamber 39A, causing the secondary chamber 39B to at least partially collapse. Movement of the gel or fluid assists the interior bag 22 in achieving more rapid shape change, to thereby achieve more rapid focus. The secondary chamber(s) 39B is located off of the optical axis of the interior bag 22 to maintain a clear light path through the interior bag 22.

Figure 8:
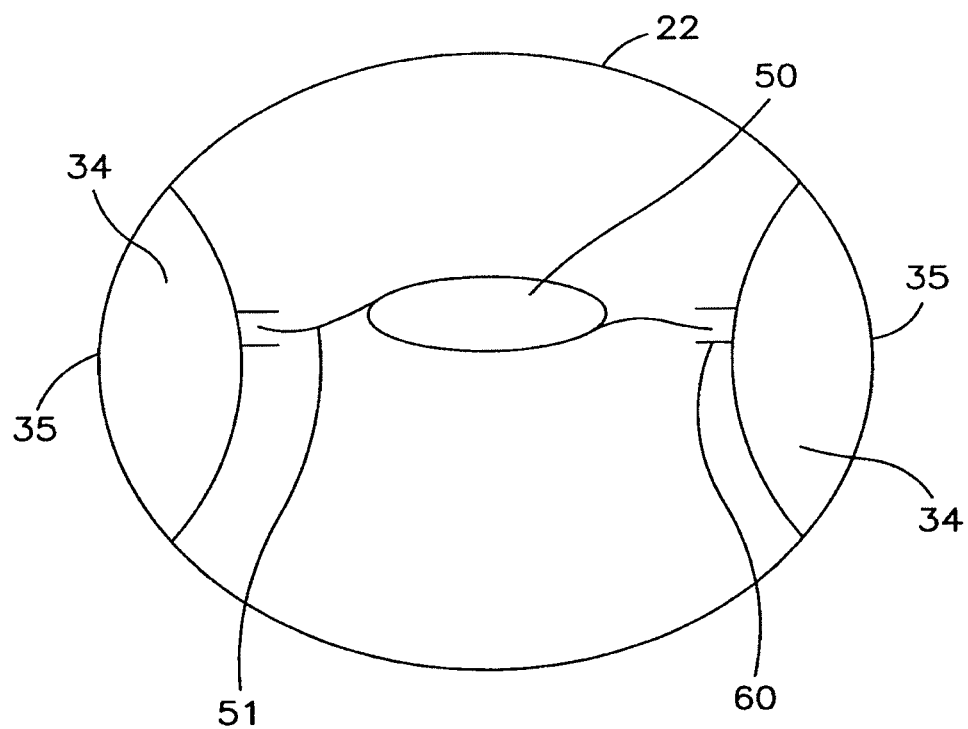
FIG. 8 illustrates a further embodiment of the interior bag adapted to hold a quantity of a time release pharmaceutical.

FIG. 8 illustrates an embodiment of the interior bag 22 having one or more separate chambers, shown here as a single annular chamber 34, for holding a quantity of a time release pharmaceutical agent for treating diseases of the eye, for example, glaucoma or infection. The chamber 34 is filled with the pharmaceutical agent after the interior bag is inserted into the capsular bag of the eye. The pharmaceutical agent is released into the capsular bag and the eye over time through a permeable wall section 35 of the interior bag 22, with the permeability of wall section 35 being controlled to permit the pharmaceutical to pass through the wall section 35 at the desired rate.

Figure 9:
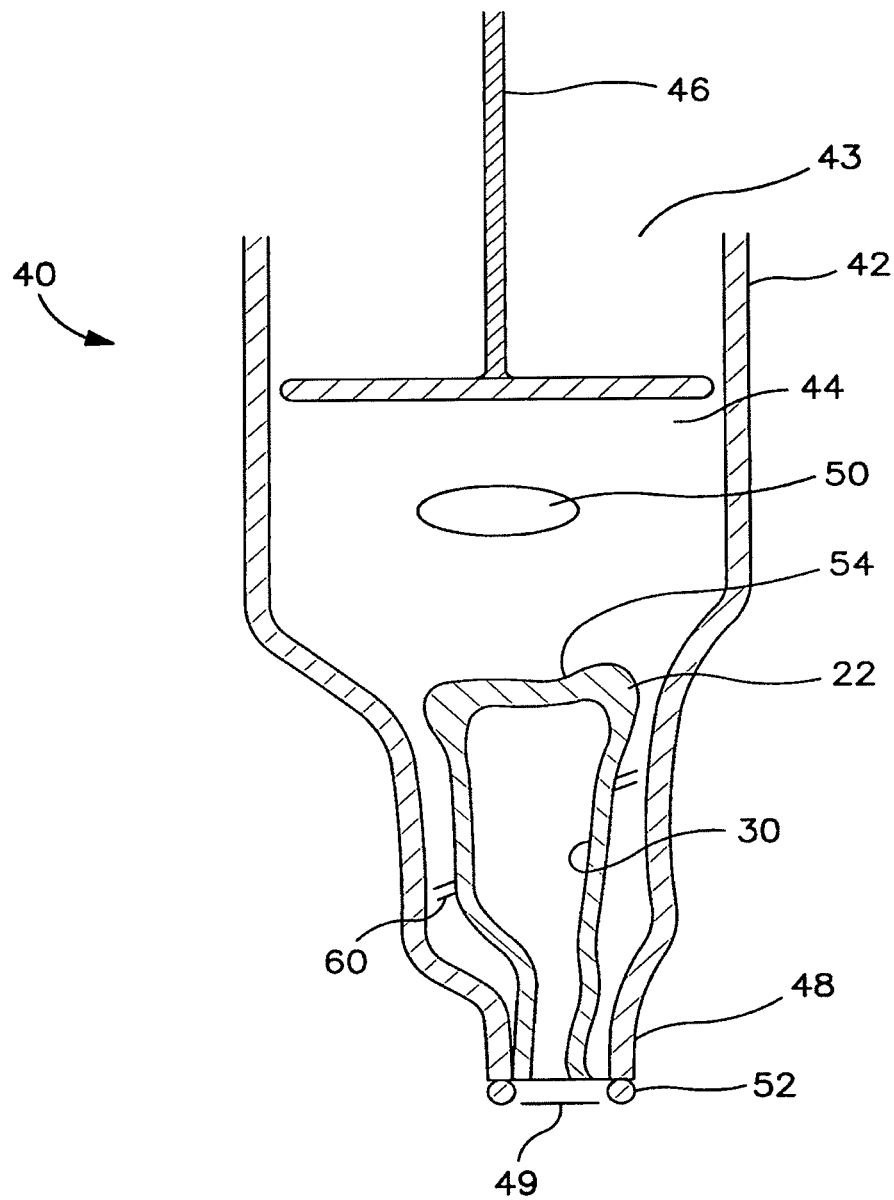
FIGS. 9 and 10 illustrate cross-sectional views of injectors with an interior bag ready for insertion into a capsular bag.
Figure 10:
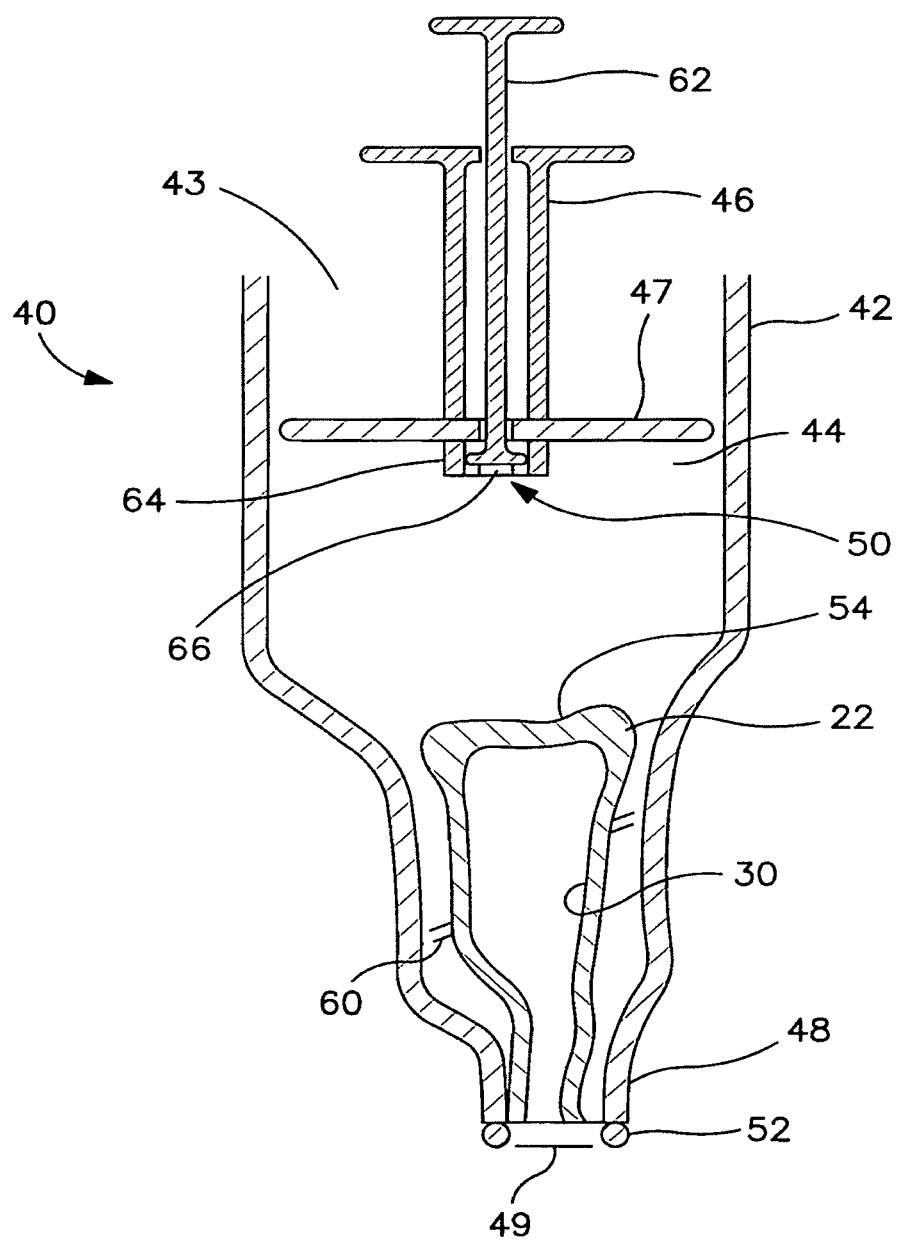

FIGS. 9 and 10 illustrate injectors for inserting the interior bag 22 into the capsular bag of the human eye. In FIG. 9, the injector 40 is comprised of a housing 42 that is adapted to hold the interior bag 22. A plunger 46 with a piston 47 is inserted into the open proximal end 43 of the housing 42. The housing 42 functions in part as a fluid containment reservoir 44 for a pressurizing fluid and is tapered at its distal end 48 and terminates in an opening 49 having a diameter of about 1.0 to 3.0 mm. The interior bag 22 is inverted such that the exterior surface 30 of interior bag 22 is on the inside of the bag. The bag 22 is held at the distal end 48 of the injector 40 by a roll 52 that is similar to the opening of a balloon. The interior bag 22 closes the distal end 48 of the injector 40. The roll 52 squeezes itself against the distal end 48 of injector 40. The pressurizing fluid is a surgical fluid or optical fluid or gel or lubricant and preferably may be Healon, saline, water, sodium hyaloramic, lynocaine, or any other suitable surgical or optical fluid, gel or lubricant. The plunger 46 pressurizes the fluid in the fluid containment reservoir 44. The plunger 46 and piston 47 allows a surgeon to selectively increase or decrease the volume of the fluid containment reservoir 44. While a refractive device 50 in the form of a soft IOL is shown in the reservoir 44, the fluid or gel itself, also contained in the reservoir 44, could serve as the refractive device in the case of an injectable lens.

Using the injector of FIG. 9 in a surgical procedure requires that the interior bag 22 be inserted into the open end of housing 42 and attached thereto by slipping the roll 52 over the distal end opening 48 of the housing. The housing is then filled with a surgical or optical fluid or gel or lubricant. If a soft IOL is to be implanted, for example, an IOL formed of a hydrogel material, the IOL may then be inserted into the fluid containment reservoir 44; otherwise the fluid or gel in the reservoir 44 forms the refractive device in the case of an injectable lens.

In order to insert the interior bag 22 into the capsular bag 26 of the human eye 28, the inside surface 54 of the interior bag 22 is pressurized by moving the plunger 46 and piston 47 from a first position to a more distal second position. Applying pressure to the interior bag 22 causes the interior bag 22 to invert and move through the opening 49 at the distal end 48 of the injector 40 and into the capsular bag 26 through an incision 29 (FIG. 1) in the eye, the incision 29 being made through the side of the cornea off of the visual axis.

The interior bag 22 enters the incision 29 in the eye 28 as it moves through the distal end 48 of the injector 40. As the interior bag 22 passes through the opening 49 at the distal end 48 of the injector 40, the interior bag inverts or turns itself inside out and orients itself inside the capsular bag 26. This is apparent when viewing FIGS. 1 and 9 together.

As noted, pressurizing the inside surface 54 of the interior bag causes the interior bag 22 to collapse inside the fluid containment reservoir and then invert and move through the opening end 49 at the distal end 48 of the injector 40, through the incision 29 and into the capsular bag 26. It should be noted that the volume of fluid or gel injected into the interior bag 22 should be monitored to ensure that the interior bag's volume does not exceed the volume of capsular bag 26. Filling interior bag 22 with the optical fluid or gel causes enough curvature for achieving an index of refraction as a result of the curvature of the interior bag 22, as well as the volume of optical fluid contained within interior bag 22, to obtain the desired refraction.

If a soft IOL 50 is to be implanted, the IOL is transported by the fluid or gel flow and is squeezed through opening 49 and incision 29 into the interior bag 22. As this occurs, the roll 52 remains attached to the distal end 48 of the injector 40, and the interior bag 22 and refractive device 50 are oriented by the surgeon to the position shown in FIG. 1.

To create the closed system inside the interior bag 22, the roll 52 is unrolled. Unrolling the roll 52 allows a surgeon to have slack in the end of the roll to work with. This is important because the surgeon must next glue the ends of the roll 52 together to fully close the interior bag 22. The surgeon may, for example, use a fibrinogen and thrombin combination to make a fibrin glue. After the closed system is created, the excess of the unrolled end of the bag 22 is removed or trimmed and the interior bag is secured by positioning and friction fitting the irregularly contoured outer surface 30 of the interior bag 22 with the inside surface 24 of the capsular bag 26. The friction fit should occur naturally, as the interior bag 22 is filled and pressurized to the extent that it fits the capsular bag 26. Finally, the surgeon closes the surgical incision.

FIG. 10 illustrates an embodiment of the injector 40 for use with an IOL that is too hard or cannot otherwise be squeezed through opening 49 and incision 29. This form of the injector 40 has a secondary plunger and piston assembly 62 coaxial with, and movable relative to, plunger 46 and piston 47. The piston of secondary plunger and piston assembly 62 may either be the flat end of the plunger or an enlarged flat surface formed thereon, as illustrated in FIG. 10. Piston 47 has a cup shaped recess 64 formed in its distal surface for removably holding a soft IOL which has been folded, as shown at 66, to a size that will permit insertion through the opening 49 and incision 29 and into the capsular bag 26 of the eye. In this embodiment, the interior bag 22 is positioned inside the housing 42 of the injector 40 (as described above). Surgical or optical fluid is placed in the fluid containment reservoir 44. The soft IOL 66 is folded and inserted into the recess 64 on piston 47 and the plunger 46 and piston 47 containing folded IOL 66, together with coaxial plunger and piston assembly 62, is placed in fluid communication with the housing 42. To insert the interior bag 22 and the folded IOL 66, plunger 46 and piston 47 are depressed to move it in a distal direction in reservoir 44. Pressurizing the fluid in reservoir 44 collapses and inverts interior bag 22 as previously described and forces it through the opening 49 and incision 29. Plunger and piston assembly 62 is moved distally to force the folded IOL 66 from recess 64 and through the opening 49 and incision 29 into the interior bag 22 and the haptics of the IOL are fitted into supports 60. As illustrated, IOL supports 60 are offset relative to each other so that they will align after the interior bag 22 is inserted into the capsular bag 26 from the side of the eye and is then positioned to receive the IOL 50. It should be recognized that the refractive device 50 or 66, both in this embodiment and the embodiment shown in FIG. 9, may also be placed/injected by the surgeon as a separate procedure after the interior bag 22 is placed into the capsular bag 26.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, the method of the invention is described in a series of steps described in a preferred order, but the most important aspect is not the actual order of the steps, but the end result, enabling an interior bag 22 to be forced out of injector 40 with the use of pressurizing fluid. Thus, the breadth and scope of the present invention should not be limited by any of the above-described exemplary embodiments, but should be defined only in accordance with the following claims appended hereto and their equivalents.

What is claimed is:

1. An internal eye apparatus, comprising:
   an injectable interior bag configured to contain a refractive device, the interior bag having an outer surface configured to engage an inner surface of a capsular bag of an eye to allow a partial fluid flow between the inner surface of the capsular bag and the outer surface of the interior bag in a manner reducing a probability of posterior capsular opacification in the eye,
   wherein the interior bag is squeezable for insertion into the capsular bag and expandable to substantially occupy the capsular bag once inserted.

2. The apparatus of claim 1, wherein the refractive device includes a liquid gel.

3. The apparatus of claim 1, wherein the refractive device includes a solid lens.

4. The apparatus of claim 1, wherein the outer surface of the interior bag includes protrusions configured to engage an inner surface of the capsular bag of an eye.

5. The apparatus of claim 1, wherein the injectable interior bag is an optically clear, biologically-compatible bag.

6. The apparatus of claim 1, wherein the interior bag is semi-permeable.

7. The apparatus of claim 1, wherein the interior bag is impermeable.

8. The apparatus of claim 1, wherein the outer surface of the interior bag includes projections configured to maintain the interior bag in a relatively constant position with respect to the capsular bag of the eye.

9. The apparatus of claim 8, wherein the projections include one or more humps, angled edges, squared edges, beads, corners, or a combination of two or more thereof, configured to engage the interior bag to the inner surface of the capsular bag of the eye.

10. The apparatus of claim 8, wherein the projections are positioned on the interior bag to engage the interior surface of the capsular bag of the eye at approximately a midpoint of the capsular bag.

11. The apparatus of claim 8, wherein the projections are positioned on the interior bag to engage the interior surface of the capsular bag of the eye above, below, or above and below a midpoint of the capsular bag of the eye.

12. The apparatus of claim 1, wherein the refractive device has an index of refraction in a range of about 1.43 to 1.46.

13. The apparatus of claim 1, wherein the refractive device is a compressible disc lens.

14. The apparatus of claim 1, wherein the refractive device includes at least one intraocular lens (IOL) having two or more haptics.

15. The apparatus of claim 1, further comprising:
   a bridge structure formed inside the interior bag and configured to hold the refractive device.

16. The apparatus of claim 15, wherein:
   the refractive device includes at least one intraocular lens (IOL) having two or more haptics that fit between and engage opposed surfaces of the bridge structure to hold the IOL in place inside the interior bag, and the bridge structure is configured to transfer pressure applied to the interior bag from the capsular bag to the IOL to achieve accommodation.

17. The apparatus of claim 16, wherein the refractive device includes a plurality of IOLs.

18. The apparatus of claim 1, wherein:
the refractive device includes a gel or other optical fluid lens,
the interior bag includes multiple chambers, including a main chamber and at least two secondary chambers,
the gel or other optical fluid lens fills the main chamber to constitute the refractive device, and
each secondary chamber includes an opening to the main chamber to enable accommodative fluid flow between the main chamber and secondary chambers in response to forces applied from the capsular bag of the eye.

19. The apparatus of claim 1, wherein:
the interior bag includes at least one separate chamber configured to hold a pharmaceutical agent, and
the separate chamber includes a permeable wall section to permit the pharmaceutical agent to pass through the permeable wall section at the predetermined rate.

20. Interior bag eye implantation kit, comprising:

an injectable interior bag configured to contain a refractive device, the interior bag having an outer surface configured to engage an inner surface of a capsular bag of an eye to allow a partial fluid flow between the inner surface of the capsular bag and the outer surface of the interior bag in a manner reducing a probability of posterior capsular opacification in the eye; and an injector having configured to house the interior bag in a compressed form and to enable injection of the interior bag into the capsular bag, wherein it expands to substantially occupy the capsular bag, the injector comprising:

a housing adapted to hold the compressed interior bag and a pressurized fluid in a fluid containment reservoir; and a plunger configured to eject the fluid from the fluid containment reservoir and the interior bag into the capsular bag of the eye.

* * * * *